(12) United States Patent
Marcon et al.

(10) Patent No.: US 6,619,300 B2
(45) Date of Patent: Sep. 16, 2003

(54) FLAVOR ENHANCED PROTECTIVE DENTAL FLOSS

(76) Inventors: Robert Victor Marcon, 3471 Sinnicks Avenue, Niagara Falls, Ont. (CA), L2J 2G6; Lawrence Wayne Nash, 17 Beachview Drive, St. Catharines, Ont. (CA), L2N 3W2

( * ) Notice: Subject to any disclaimer, the term of this patent is extended or adjusted under 35 U.S.C. 154(b) by 0 days.

(21) Appl. No.: 10/023,356

(22) Filed: Dec. 17, 2001

(65) Prior Publication Data

US 2002/0074012 A1 Jun. 20, 2002

Related U.S. Application Data

(60) Provisional application No. 60/255,823, filed on Dec. 18, 2000.

(51) Int. Cl.⁷ .............................................. A61C 15/00
(52) U.S. Cl. ........................ 132/321; 132/200; 424/49
(58) Field of Search ................................ 132/321, 323, 132/324, 325, 326, 327, 328, 329, 200; 424/52, 58, 48, 53, 49

(56) References Cited

U.S. PATENT DOCUMENTS

| | | | | |
|---|---|---|---|---|
| 3,838,702 A | * | 10/1974 | Standish et al. ............ | 132/321 |
| 3,897,795 A | * | 8/1975 | Engel .......................... | 132/321 |
| 3,943,949 A | * | 3/1976 | Ashton et al. ............... | 132/321 |
| 4,983,404 A | * | 1/1991 | Raman et al. ................. | 426/3 |
| 5,357,990 A | * | 10/1994 | Suhonen et al. ............ | 132/321 |
| 5,607,681 A | * | 3/1997 | Galley et al. ............... | 424/405 |
| 5,695,745 A | * | 12/1997 | Barton et al. ................. | 424/49 |
| 5,880,076 A | * | 3/1999 | Vermeer ...................... | 510/123 |
| 5,967,153 A | * | 10/1999 | Mitha et al. ................ | 132/321 |
| 5,967,155 A | * | 10/1999 | Marcon ..................... | 132/321 |
| 6,080,481 A | * | 6/2000 | Ochs et al. ................. | 428/372 |
| 6,145,516 A | * | 11/2000 | Guay et al. ................. | 132/321 |
| 6,197,288 B1 | * | 3/2001 | Mankoo .................... | 424/76.1 |

* cited by examiner

*Primary Examiner*—Kevin Shaver
*Assistant Examiner*—David C. Comstock

(57) ABSTRACT

The present invention relates to a flavor enhanced protective dental floss comprising a dental floss and various dental desensitizing formulations that taste good. Regular use of such a flavor enhanced protective dental floss will therefore provide not only a significant reduction in the incidence of dental hypersensitivity but also provide all other benefits normally associated with flossing. As a result, consumers will now be able to achieved better overall results; inexpensively, safely, and in a much more pleasurable manner than is otherwise possible.

21 Claims, No Drawings

FLAVOR ENHANCED PROTECTIVE DENTAL FLOSS

CROSS-REFERENCE

This application claims priority from U.S. Provisional Application, serial No. 60/255,823, filed Dec. 18, 2000.

FEDERALLY SPONSORED RESEARCH OR DEVELOPMENT STATEMENTS

Not applicable.

REFERENCE TO A MICROFICHE APPENDIX

Not applicable.

BACKGROUND OF THE INVENTION

This invention relates to dental flosses and, specifically, to flavour enhanced protective dental flosses (FEPD flosses) which reduce dental decay, dentinal hypersensitivity, and also taste remarkably good.

It is generally recognized by the dental profession that plaques, including those that are found between the interproximal surfaces of teeth, are a major cause of both dental decay and inflammatory periodontal disease. These plaques, which can contain 250 or more separate microbial species, use sugars and other fermentable carbohydrates to produce polymers which bind the organisms to the surface of teeth and acids which cause their demineralization. In the first stages, a carious lesion does not contain an actual cavity but with prolonged and repeated demineralization by these plaque created acids, a cavity will form. Thus, each time something sweet is consumed plaques produce approximately 20 minutes of oral acid which, in turn, seriously contributes to dental demineralization.

Furthermore, plaques, if not removed will in time form calculus, and calculus, is the mineralized bacterial plaque deposits found on teeth, restorations, and other solid oral structures. Invariably, calculus is covered by a film of plaque, the organisms of which also occupy its porous structure. Its composition is generally made up of seventy percent organic salts, and a thirty percent combination of micro-organisms and organic material. Moreover, its formation is always preceded by plaque accumulation which serves as an organic matrix for the subsequent mineralization of the deposit. Mineralization, by the precipitation of the mineral salts in plaque can start at any time from the second to the fourteenth day of plaque formation, but some individuals can begin to calcify plaque in four to eight hours. Initially, small crystals develop close to these bacteria. Then, gradually, the intermicrobial matrix becomes entirely calcified and eventually the bacteria itself also becomes mineralized.

As a result, the presence of calculus not only makes effective oral hygiene impossible but can also seriously irritate gum tissues. Thus, its prevention and or removal to help control the inception or progression of inflammatory periodontal disease is of great importance. It is also the reason why dental professionals have always recommended flossing, in addition to the conventional practice of using a brush and dentifrice, for flossing clears the interproximal surfaces of the teeth in a manner that a toothbrush, with or without a dentifrice, cannot achieve. With this two step cleaning method effective oral hygiene is, therefore, greatly improved.

In addition to the various problems created by plaques it has also been estimated that as many as one in seven people in the population have suffered from dentinal hypersensitivity at some time. Treatments for this condition are, however, only available from professional dental practitioners, certain dentifrices, some mouthwashes, and one floss. Unfortunately, professional dental practitioners are invariably expensive, time consuming, and not always effective, whereas, a brush and dentifrice alone are ineffective in cleaning, let alone therapeutically treating, the interproximal surfaces of teeth. Mouthwashes have been suggested by the prior art but as yet no commercial products have been realized that can efficiently clean interproximal dental surfaces or provide any notable relief. A dental desensitizing floss has also been suggested by the prior art—specifically U.S. Pat. No. 5,967,155. However, this floss, while effective, releases only modest levels of flavouring.

As a result, there is currently a large deficiency with contemporary remedies in providing satisfactory means that work and taste good. In consequence, the invention detailed herein addresses these failings by providing a more effective and desirable solution than can be currently achieved.

OBJECTS AND ADVANTAGES

The invention disclosed herein overcomes many of the drawbacks listed in the prior art while also providing a more effective solution and improved performance over presently used dental flosses. In addition, some of the objects and advantages associated with this invention are described below. Others will become apparent as the description proceeds.

Objects:
(1) To provide various formulations, for use upon dental flosses, that are not only highly effective at reducing dentinal hypersensitivity but also taste good.
(2) To provide a new and improved method of making said formulations.
(3) To help reduce oral plaques and the dental problems they cause.

Advantages:
(1) Utilizing a flavour enhanced protective dental floss with one or more dental desensitizing agents can help diminish dentinal hypersensitivity.
(2) The delivery of the dental desensitizing agents to the interproximal surfaces and subgingival areas of the teeth is superior to any brush and dentifrice or mouthwash presently available.
(3) The enhanced flavour characteristics of a flavour enhanced protective dental floss is superior to any other similar floss currently available.
(4) Fluoride based compounds may be used within the flavour enhanced protective dental floss to significantly reduce the incidence of dental decay.
(5) The flavour enhanced protective dental floss may make use of various abrading or pigmenting agents in order to provide cleaner dental surfaces or whiter teeth, respectively. Moreover, cleaner dental surfaces will not only reduce dental decay but will also increase the therapeutic effectiveness of dental desensitizing agents, fluorides, and other medicaments.
(6) Professional dental personnel are not required to administer any of these medicaments. This not only reduces time but cost as well.
(7) The ingredients employed by the flavour enhanced protective dental floss of this disclosure are cost competitive.

(8) The cost and mechanics of incorporating into the flavour enhanced protective dental floss the various ingredients disclosed herein are both inexpensive and technically favourable.

SUMMARY OF THE INVENTION

The invention disclosed herein details a flavour enhanced protective dental floss which can reduce dental plaques and the pain associated with dentinal hypersensitivity. Moreover, the enhanced flavour characteristics of this new floss are not only exceptional but long lasting as well.

To begin, dental plaques, which can contain 250 or more separate microbial species, use sugars and other fermentable carbohydrates to produce polymers which binds them to the tooth surface and acids which cause dental demineralization. In time, these plaques will produce caries and form calculus. The establishment of calculus can seriously irritate gum tissues and so promote the advance of periodontal disease. Do to its porous structure calculus can also harbour a multitude of bacterial plaques and so promote its continued spread. This makes effective oral hygiene impossible. Dental plaques are also capable of producing various offensive odours which, while not harmful, are self-evident in their undesirability.

In addition to plaques, dentinal hypersensitivity is a very painful disorder which, by current estimates, as many as one person in seven will bear at some point. The principle theory to explain this mechanism of pain transmission from the dentine to the pulp is called the, "Hydrodynamic Theory". It is a theory based upon the observation that fluid within the dentinal tubules of the dentine can flow either inward or outward depending on the pressure variations in the surrounding tissues. Pain is, therefore, created by the rapid movement of fluid in the open dentinal tubules that stimulate, at the dentinal-pupal junction, the free nerve endings from the pulp.

A flavour enhanced protective dental floss, however, addresses these problems by administering various highly effective dental desensitizing formulations to and around the interproximal surfaces and subgingival areas of teeth. In addition, floss formulations prepared using a Staged Preparation Technique offers consumers a product that not only tastes remarkably good but is also long lasting. In turn, this makes flossing a much more pleasurable experience than would otherwise be possible.

Fluorides can also be employed within these formulations in order to reduce dental decay as well as other ingredients or compounds. These substances may therefore include, polishing and abrading agents, peroxide based compounds, and pigmenting agents, used alone or in combination.

As a result, a flavour enhanced protective dental floss can offer many benefits. It can, for example, diminish dental plaques and other related dental diseases as well as the pain or discomfort associated with sensitive teeth. Cosmetically, teeth will tend to be whiter and appear healthier. Taste has also been greatly improved over and above any other similarly produced product and, in final summation, all of this can be accomplished in a manner that is convenient, inexpensive, and safe.

BRIEF DESCRIPTION OF THE DRAWINGS

Not applicable.

DETAILED DESCRIPTION OF THE INVENTION

Introduction

The present invention pertains to a flavour enhanced protective dental floss or FEPD floss that not only tastes good but which can also be used to help reduce the incidence of or the effects associated with dentinal hypersensitivity and dental plaques. While these objectives are obviously desirable they are achieved in a most unique and novel manner by including, in the FEPD floss, various specialized ingredients. In addition, by utilizing a Staged Preparation Technique these ingredients can be blended into various formulations that are not only highly effective but good tasting as well.

As such, it is to this end that the following description is therefore provided to enable any person skilled in the art to make and use the invention herein disclosed. Various modifications, however, will remain readily apparent to those skilled in the art, as the generic principles of the present invention have been defined herein specifically to provide for the description of a FEPD floss.

That said, a FEPD floss of the present invention begins with a basic or root structure that comprises at least one suitable or commercially available dental floss, binder, emulsifying agent, dental desensitizing agent, polishing or abrading agent, flavouring agent, and sweetening agent. If desired, one or more fluoride compounds may also be used. While other ingredients may also be added to achieve other effects, these primary compounds will form the basic or root formulations used herein. However, it must also be understood that all ingredients, compounds or components, regardless of the final formulation used, must be safe, present no danger to the body, teeth or soft tissues of the mouth nor create a discolorment in their appearance. Moreover, they should be inexpensive, easy to use and apply, non-irritating, and require minimal application time. Their individual procurement may also be derived from either natural or synthetic sources or a combination thereof so as to maximize formulation flexibility and manufacturing logistics.

With these thoughts in mind, the description will now individually detail these root components first, in order to more fully explain their individual compositions, applications, and functions. Thereafter, the description will detail various additional components, novel formulations and balancing methods thereof, Staged Preparation Techniques, and finally end with the addendum.

Dental Flosses

The meaning of the words, "dental floss(es)", shall be herein understood to include both dental flosses and dental tapes as well as any other similar article. Moreover, the dental flosses and tapes used in the present invention may include any suitable or commercially available dental floss or tape. These flosses and tapes can also be fabricated from either natural or synthetic sources examples of which include, but are not limited to, filaments or yarns of high and normal tenacity polymers, nylons, polyolefins, polyethylenes, polypropylenes, fluorocarbon compounds, polytetrafluoroethylenes, rayons, dacrons, acrylics, acetate polymers, and other plastics alone or in combination. Natural substances may include, but are not limited to, cotton, wool, silk, linen, and other staple fibres alone or in combination. Blends of synthetic-natural fibres can also be used. However, synthetic filaments are preferred for they are more durable, stronger, generally less expensive, and easier to work and procure.

The length, diameter, structure or design of the floss itself is also not limited to any specific size, shape, arrangement or configuration and thus, can be fabricated to suit any specific intention. It can, for example, be composed of a plurality of individual filaments that have been formed together to give a larger thread having a sufficiently small diameter to permit insertion between the teeth. It can also comprise a composite multifilament yarn bonded to an extruded monofilament or to another multifilament yarn. A single circular, square or rectangular shaped monofilament thread is also useful. Other suitable variations are also well known in the art and as such are also useable in the invention disclosed herein.

Binders

Binders are used in the invention disclosed herein to bind or otherwise attach to a dental floss the ingredients herein specified by this disclosure. They also provide the ability to alter the frictional characteristics of dental floss as well as help bind together the individual filaments comprising the floss itself. Moreover, the varieties used herein are not restricted to any specific types or compositions and are thus, given great freedom in their formulations, structures or make-ups. Examples of some suitable binders may therefore include, but are not limited to, natural waxes from insects, animals or plants, synthetic waxes, petroleum waxes such as polyethylene glycol wax, microcrystalline wax, liquid polyethylene glycol esters of beeswax as well as other water soluble or non-water soluble wax or wax-like compounds, or water soluble or non-water soluble polymers, soaps, gums, resins, and other substances known in the art.

Emulsifying Agents

All FEPD flosses must make use of one or more emulsifying agents which may include, but are not limited to, sorbitan monostearate, polysorbate 60, and the like, alone or in combination. Their use, within the formulations listed below, will allow individual chemical compounds to better interact, disperse, and disseminate during production as well as spread upon various dental surfaces in a much more efficient and effective manner. In turn, this makes the final product not only better but more consistent as well.

However, it must also be noted that while sorbitan monostearate and polysorbate 60 may both be used within a given formulation they must never be blended, mixed or combined simultaneously. That is because it makes certain ingredients clump together or react in various other undesirable ways.

Dental Desensitizing Agents

It has been estimated that as many as one in seven people have suffered from dentinal hypersensitivity at some time. In the United States this figure has ranged as high as forty (40) million adults—ten (10) million of which endure chronic hypersensitivity. Hypersensitivity is most common among patients aged twenty to forty years with the affliction peaking in the thirties. The condition has also been reported to occur slightly more often in females than males, however, this finding has not been statistically significant. As a result, these figures clearly demonstrate the magnitude and scope of the affliction and suffering manifested by it.

As an affliction, dentinal hypersensitivity can be simply defined as an adverse reaction or pain in one or more teeth resulting from a thermal, chemical, or mechanical stimulus. However, microscopic examination of clinically hypersensitive surfaces has shown that areas where the dentine has been exposed by gingival recessions, defective restorations, caries, periodontal therapy, loss of enamel through poor diet, fractures, toothbrush abrasion, occlusal wear, cementum loss from abrasion or erosion, or parafunctional habits can promote sensitivity. Bulimics may also experience extreme dentinal hypersensitivity because of the significant enamel destruction caused by stomach acids during periods of induced vomiting.

In cases such as these, the tubules, of which there are millions, have been shown microscopically to be generally wider and more numerous than in nonsensitive areas. Moreover, hypersensitive dentine is found almost exclusively on the facial surfaces of teeth at the cervical margins with the relative sensitivity frequency of individual teeth being reported as follows: premolars 38 percent, incisors 26 percent, canines 24 percent, and molars 12 percent.

Medically, the principle theory to explain the mechanism of pain transmission from the dentine to the pulp is called the, "Hydrodynamic Theory", and it was originated by Kramer and later expounded on by Alfred Gysi. Briefly stated, the theory is based upon the observation that dentine consists of hollow tubules which are filled with fluid secreted by the pulp. These fluids are not static and so can flow either inward or outward depending on the pressure variations in the surrounding tissues. Moreover, each dentinal tubule contains a cytoplasmic cell process that extends from the odontoblast cell body at the edge of the pulp. In young teeth, the process extends to the dentinoenamel or dentinocemental junction. In older teeth, the processes may have withdrawn thus helping explain why younger people experience more pain. In addition, the odontoblast cell bodies lie side by side, at the dentinal-pulpal junction, with nerve endings from the pulp. Some of these nerve endings will also extend short distances into the dentinal tubules. When, therefore, any surface simulation causes a rapid flow of fluid within these tubules it may subsequently stimulate the free nerve endings from the pulp and so elicit a painful sensation. Such stimuli, which can include thermal, chemical or mechanical, will further increase the sensation of pain if enamel thicknesses have been reduced or portions of the dentine have been uncovered to expose the dentinal tubules. The theory of hydrodynamics, thus clarifies how so many different stimuli can elicit the same pain response.

If, then, the greatest pain sensations are felt when fluid in the dentinal tubules flows either inward or outward then the occlusion of these tubules should significantly reduce this fluid flow. In turn, this should diminish the sensation of pain accordingly. Alternately, desensitizing the free nerve endings at the dentinal-pulpal junction should also cause a similar reduction in pain.

With these thoughts in mind the invention disclosed herein will endeavour to achieve a reduction in the pain associated with dentinal hypersensitivity by the incorporation of one or more dental desensitizing agents into the FEPD floss. These desensitizing agents will strive to occlude the dentinal tubules or desensitize the free nerve endings from the pulp. Furthermore, these ingredients should be safe, inexpensive, easy to use and apply, non-irritating, require minimum application time, and present no danger to the body, teeth or soft tissues of the mouth nor create any discolorment in their appearance.

As a result, suitable desensitizing agents may therefore include, but are not limited to, nitrate based compounds such as potassium nitrate, sodium nitrate, lithium nitrate, magnesium nitrate, calcium nitrate, strontium nitrate, as well as sodium citrate, dibasic sodium citrate, dibasic sodium citrate in a pluronic gel, strontium chloride, calcium hydroxide, dibasic calcium phosphate, strontium acetate and sodium monofluorophosphate, formaldehyde, and the like, alone or in combination.

Polishing Or Abrading Agents

One or more polishing or abrading agents may also be utilized in a FEPD floss. Moreover, the type and quantity of abrading agents employed are not restricted to any specific variety or amount. This, therefore, allows the polishing and abrading agents used to better suit the final effects desired.

In any case, their incorporation will help clean and polish teeth and so help produce a smooth and shiny surface that will resist discoloration, bacterial accumulation, and retention. Cleaner teeth also help to improve the therapeutic performance of other ingredients such a fluorides as well as reduce the overall effects of oral acids and related demineralizations.

Thus, with these thoughts in mind, a FEPD floss may make use of one or more polishing or abrading agents which may include, but is not limited to, a boride, carbide, carbonate, bicarbonate, nitride, oxide, dioxide, phosphate, silicate or sulphide of such elements as aluminum, calcium, iron, magnesium, potassium, silicon, sodium, tin, titanium, tungsten, zinc, and zirconium, alone or in combination.

While sodium bicarbonate may therefore be used as a mild, safe, and inexpensive abrading agent its usefulness does not end there. It can, for instance, also function as an anti-odorant, and so offer some odour absorbing capabilities. Being a water soluble alkaline compound it also has the ability to neutralize some quantities of oral acids. It also has the ability to act as a disinfectant by releasing, during its decomposition, modest quantities of elemental oxygen. Moreover, the amount of sodium bicarbonate used within an FEPD floss may be adjusted to suite any specific taste, texture or formulation required. In some recipes it may even be desirable to omit its use altogether or conversely, the manufacturer may employ copious quantities to amplify its effects.

Moreover, it has also been discovered, by the inventors herein, that the independent use of most salts produce extremely undesirable oral tastes. For example, the independent use of potassium nitrate or sodium bicarbonate within a formulation generates extremely unpleasant sensorial effects. However, the inventors have also noted that the combination of two dissimilar salts, i.e. potassium nitrate and sodium bicarbonate in a respective ratio of approximately 1 to 3, virtually negates these effects. Consequently, the use of this new discovery therefore allows a formulation's existing flavouring agents to achieve a much better result than would otherwise be possible.

Though sodium bicarbonate is a preferential compound there may be instances where it may be necessary or desirable to substitute one or more alternate compounds in its place. Such times may arise, for example, when certain compounds utilized within a given formulation chemically interact with sodium bicarbonate in an undesirable manner. Nonetheless, these alternate substances, though less preferable than sodium bicarbonate, should still be water soluble and possess traits similar to those found in sodium bicarbonate. Such a compound may, therefore, include potassium bicarbonate. The exact solubility and alkalinity of potassium bicarbonate will vary from that provided by sodium bicarbonate but this can be compensated by varying the respective amount used. It can also be used alone or in combination with sodium bicarbonate, and blended or otherwise incorporated into a FEPD floss in a fashion similar to that of sodium bicarbonate.

Flavouring Agents

FEPD flosses may also utilize one or more flavouring agents. These may comprise essential oils, synthetic flavours, or mixtures thereof including, but not limited to, oils derived from plants and fruits such as citrus oils, fruit essences, mint, peppermint oil, spearmint oil, clove oil, oil of wintergreen, anise, sassafras, sage, eucalyptus, marjoram, cinnamon, lemon, orange, banana, cherry, apple, pineapple, grape, strawberry, blueberry, tutti frutti, methyl salicylate, Hagelin flavouring #640047, Hagelin flavouring #640057, Hagelin flavouring #671009, Hagelin flavouring #671010, and the like. Those skilled in the art will recognize that natural and artificial flavouring agents may be used independently or combined in any sensorially acceptable blend. All such flavours and flavour blends are contemplated by the present invention. However, it should also be noted that liquid based flavourings are preferred over powdered varieties as they tend to blend more easily with other ingredients and substances.

Sweetening Agents

To foster greater consumer appeal FEPD flosses may also contain one or more natural or artificial sweetening agents, alone or in combination. These may include, but are not limited to, sucrose, lactose, dextrose, maltose, dextrin, dried inverted sugar, fructose, levulose, galactose, corn syrup and their solids, sorbitol, mannitol, xylitol, hydrogenated starch hydrolysates, maltitol, sucralose, aspartame, salts of acesulfame, alitame, saccharin and its salts, cyclamic acid and its salts, glycyrrhizin, dihydrochalcones, thaumatin, monellin, and the like. Though any type or blend of sweetener may be used artificial compounds are preferred for they substantially reduce the potential for cariogenic decay.

Fluorides

Fluorides have in the past been found to help prevent the incidence of carious lesions or caries. Caries are caused when teeth demineralize at a rate faster than they remineralize and most demineralization is caused by acid producing dental plaques. Remineralization, however, is promoted by calcium and phosphate, the chief remineralizing agents found also in saliva. Fluoride based compounds, therefore, provide protection from carious lesions or caries by acting as a catalyst to speed the precipitation of calcium phosphate, in the form of a hydroxy apatite, onto or into teeth. However, this is not fluoride's only role. It is also able to inhibit the activity of some bacterial enzymes and their acid producing processes, and at extremely high concentrations it can also kill certain plaque bacteria. Even more important, it tends to become incorporated into the apatite, as a fluoridated hydroxy apatite or "fluorapatite", creating a mineral that is appreciably less dissolvable by acid.

Hence, FEPD flosses may contain one or more fluoride based compounds. These compounds may also be slightly soluble in water or may be fully water soluble. They are, however, foremost characterized by their ability to release fluoride ions in water and their freedom from undesired reactions with the FEPD floss's other compounds. Among these materials are numerous fluoride based compounds which can comprise inorganic fluoride salts such as soluble alkali metal, alkaline earth metal salts, and others. Examples of such include, but are not limited to, sodium fluoride, potassium fluoride, ammonium fluoride, a copper fluoride such as cuprous fluoride, zinc fluoride, sodium fluorosilicate, ammonium fluorosilicate, sodium fluorozirconate, barium fluoride, calcium fluoride, sodium monofluorophosphate, sodium silicofluoride, aluminum mono- and di-fluorophosphate, and fluorinated sodium calcium pyrophosphate. However, alkali metal fluorides, and mixtures thereof, are preferred with sodium fluoride being considered best.

When a fluoride compound is employed, the amount used is dependent to a large extent upon the type of fluorine compound, its solubility, and the final formulation and structure selected. As such, substantial leeway is given to the quantities or amounts used as long as normal formulation and pharmaceutical safeguards are observed.

Consequently, whenever fluoride based compounds are used within the formulations listed below they should amount to no more than 0.30 percent (W/W). However, it has been found that setting the maximum range at 0.24 percent (W/W) is preferable with 0.22 to 0.24 percent (W/W) being the best overall range to use.

Optimizing the effects and benefits of fluorides as well as other medicaments is also of prime importance to both manufactures and consumers alike. One way of accomplishing this is to provide as plaque free a dental enamel surface as possible. That is because most medicaments, in general, tend to function better when given a cleaner dental surface on which to work. In this respect, the incorporation into a FEPD floss of one or more peroxide based compounds, polishing or abrading agents, or other similar scrubbing or cleaning ingredients can improved results because such substances tend to attack and remove plaques. As these plaques diminish, the dental and oral impact of various medicaments will be much more effective and useful.

Peroxide Compounds

FEPD flosses may also make use of one or more peroxide based compounds such as, but not limited to, calcium peroxide, sodium carbomate peroxide, and sodium carbonate peroxide. Their use will help remove dental plaques and whiten teeth and so thereby reduce the incidence of dental caries and other related diseases. This ability to reduce dental decay stems from the fact that oxygen is released during their decompositions. Thus, when a peroxide based compound is utilized in the mouth the decomposal release of oxygen will not only vigorously attack bacterial plaques but also help whiten teeth. In addition, peroxide based compounds being mostly alkaline in nature will also help facilitate the neutralization of oral acid. Over time, as these plaques and acidic byproducts are reduced the progression of carious lesions and that of calculus accumulation upon the teeth is also substantially curtailed.

When, therefore, one or more peroxide based compounds are used, their individual concentrations will vary to some extent upon the types of peroxide compounds employed and the final formulation used in the FEPD floss. As a result, substantial leeway in both use and concentration is allowed but both the quantity as well as the level of alkalinity must be of a safe level. Assimilation of these peroxide compounds into a FEPD floss can be performed in a fashion similar to, but not limited to, that used by polishing or abrading agents.

Pigmenting Agents

FEPD flosses may also make use of one or more dental pigmenting or coloring agents. Their primary function will be to whiten interproximal and subgingival dental surfaces and to maintain this whiteness for as long as possible. Suitable pigmenting agents, however, may also be used to color the filaments or fibres comprising the floss, as a means of producing a decorative effect or as a means of signifying or designating certain formulations.

Pigmenting agents such as these may therefore be obtained from either natural or synthetic sources, or a combination thereof. Thus, by way of example and not limitation, some common available coloring agents may therefore include FD and C-type dyes and lakes, fruit and vegetable extracts, titanium dioxide, and the like, alone or in combination. However, titanium dioxide is preferred for whitening teeth because of its brilliant opaque white color and its extremely small particle size.

Though a larger size may be used, titanium dioxide particles which have been found useful in the present invention have an approximate size of 1.5 microns or less, but preferably an approximate size of 0.1 microns or less, and most preferably an approximate size of 0.04 microns or less. That is because pigmenting agents such as these are able to be absorbed or retained by the enamel and dentinal layers of the teeth and so occupy the space between the hydroxyapatite crystals or prisms that make up these layers. In this way, these small titanium dioxide particles can compete with the substances that tend to attack, stain or discolor teeth by filling the space between the prisms with an inert white material instead of an undesirable substance or coloring.

A further benefit of titanium dioxide as the pigmenting agent is its ability to also function as a mild polishing or abrading agent when it is being used. Moreover, it can also be easily incorporated into the formulations listed below by utilizing a Staged Preparation Technique or by other similar or conventional means.

Formulations

The information so far presented has given the reader the ability to produced a large number of floss formulations. With this in mind, the disclosure will now detail, using a percent weight per weight (W/W) format, four specific examples which can be used to produce the effects desired. Thus, by way of example and not limitation, the following formulations comprise:

Formulation Number One (a) one or more binders to a maximum of about 75 percent (W/W), with 41.0 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 14.6 percent (W/W) being optimal;

(d) one or more dental desensitizing agents to a maximum of about 10.0 percent (W/W), with 9.0 percent (W/W) being optimal;

(e) one or more first emulsifying agents to a maximum of about 10.0 percent (W/W), with 5.0 percent (W/W) being optimal;

(f) one or more second emulsifying agents to a maximum of about 10.0 percent (W/W), with 3.0 percent (W/W) being optimal; and (g) one or more sweetening agents to a maximum of about 1.0 percent (W/W), with 0.4 percent (W/W) being optimal.

Formulation Number Two (a) one or more binders to a maximum of about 75 percent (W/W), with 40.78 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 14.6 percent (W/W) being optimal;

(d) one or more dental desensitizing agents to a maximum of about 10.0 percent (W/W) with 9.0 percent (W/W) being optimal;

(e) one or more first emulsifying agents to a maximum of about 10.0 percent (W/W), with 5.0 percent (W/W) being optimal;

(f) one or more second emulsifying agents to a maximum of about 10.0 percent (W/W), with 3.0 percent (W/W) being optimal; and (g) one or more sweetening agents to a maximum of about 1.0 percent (W/W), with 0.4 percent (W/W) being optimal.

(h) one or more fluoride compounds to a maximum of about 0.30 percent (W/W), with about 0.22 percent (W/W) being optimal.

Formulation Number Three (a) one or more binders to a maximum of about 75 percent (W/W), with 55.6 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 3.0 percent (W/W) being optimal;

(d) one or more dental desensitizing agents to a maximum of about 10.0 percent (W/W), with 9.0 percent (W/W) being optimal;

(e) one or more first emulsifying agents to a maximum of about 10.0 percent (W/W), with 5.0 percent (W/W) being optimal; and (f) one or more sweetening agents to a maximum of about 1.0 percent (W/W), with 0.4 percent (W/W) being optimal.

Formulation Number Four (a) one or more binders to a maximum of about 75 percent (W/W), with 55.38 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 3.0 percent (W/W) being optimal;

(d) one or more dental desensitizing agents to a maximum of about 10.0 percent (W/W), with 9.0 percent (W/W) being optimal;

(e) one or more first emulsifying agents to a maximum of about 10.0 percent (W/W), with 5.0 percent (W/W) being optimal; and (f) one or more sweetening agents to a maximum of about 1.0 percent (W/W), with 0.4 percent (W/W) being optimal.

(g) one or more fluoride compounds to a maximum of about 0.30 percent (W/W), with about 0.22 percent (W/W) being optimal.

Formulations: Preferential Ingredients

The reader should also understand that while many different ingredients, compounds, and substances may be used in the above four formulations the following substances have been found to be preferable.

(1) Binders: preferably microcrystalline wax.

(2) Polishing Agents: preferably sodium bicarbonate.

(3) Dental Desensitizing Agents: preferably potassium nitrate.

(4) First Emulsifying Agents: preferably sorbitan monostearate.

(5) Second Emulsifying Agents: preferably polysorbate 60.

(6) Sweetening Agents: preferably sodium saccharin.

(7) Fluoride Compounds: preferably sodium fluoride.

Flavourings, on the other hand, are basically unrestricted as both selection and concentration are generally governed by consumer preferences, logistical availability, or cost considerations. In other words, they have no real or actual bearing upon the safety or efficacy of the final product itself. However, four flavourings have been found to be distinctive, aromatic, long lasting, and desirable. They are Hagelin flavouring #640047, Hagelin flavouring #640057, Hagelin flavouring #671009, and Hagelin flavouring #671010, used alone or in combination. As such, these four flavourings, and others like them, shall be given preferential status within this invention so as to set it apart or distinguish it from competitors. Note also, that Hagelin flavourings may be procured from Hagelin & Company, Inc., 200 Meister Avenue, Branchburg, N.J., U.S.A., 08876-6033.

Quantitative Formulation Balancing

First and foremost, the reader must clearly understand that any variances or deviations from a formulation's stated optimal figures must still be accounted for, on a similar percentage weight per weight basis, in one or more of the other components. What this means, in other words, is that a quantitative reduction or increase in the amount of flavouring used, or for that matter any other ingredient, must be accounted for by similarly or respectively increasing or decrease the quantity of one or more of the other components listed. This allows the sum of a formulation's component (W/W)s to still total 100 percent.

For example, if the flavouring used within formulation number one is reduced from 14.6 percent (W/W) to 5.0 percent (W/W) it will require a correspondingly similar increase in the amount of microcrystalline wax used. As such, the original optimal tally of microcrystalline wax must be increased from 41.0 percent (W/W) to 50.6 percent (W/W) of the formulation. This type of procedure shall, for the purpose of this disclosure, be herein referred to as Quantitative Formulation Balancing.

If a fluoride compound is also to be employed, within any of the above formulations, then the amount of microcrystalline wax used must also be quantitatively diminished by that same amount. Thus, for example, if 0.22 percent (W/W) sodium fluoride is to be utilized within formulation number one then the quantity of microcrystalline wax must be similarly or respectively reduced by that same amount and so total 41.0 minus 0.22 or 40.78 percent (W/W) of the formulation.

In most cases herein disclosed, Quantitative Formulation Balancing may be respectively achieved, on a (W/W) basis, by a similar inverse decrease or increase in the amount of microcrystalline wax employed. As such, it becomes self-evident that the purpose of microcrystalline wax is not just to provide lubrication, thread binding, and component scaffolding but formulation balancing as well.

Although microcrystalline wax may offer or yield a number of formulation balancing opportunities other ingredients may also be used. As such, two charts are conveniently provided below so that the reader may more fully understand various Quantitative Formulation Balancing techniques and the opportunities that they offer to individually tailor certain formulations to specific needs.

Quantitative Formulation Balancing (Formulations 1 and 2)

First note: a ratio of about 3:1 sodium bicarbonate to potassium nitrate must at all times be maintained within these formulations. As such, decreasing or increasing one of these ingredient's overall percentage (W/W) will force the simultaneous decrease or increase of the other so as to maintain the 3:1 ratio mentioned above.

Second note: a formulation's optimal (W/W) figures are used as the base or reference line during any Quantitative Formulation Balancing. Consequently, any ingredients added or subtracted are referenced back to this starting point.

Thirdly, the preferential substances specified below are for illustrative purposes only and thus shall not be used to limit the scope of the Quantitative Formulation Balancing technique herein disclosed.

Decreasing From Optimal:
(a) Microcrystalline wax:
   Balance by first increasing sodium bicarbonate and potassium nitrate using a 3:1 ratio as desired. If necessary increase flavouring to compensate for the rest.
(b) Sodium bicarbonate:
   Balance by first decreasing potassium nitrate to maintain a 3:1 ratio. If necessary, then add microcrystalline wax to complete balance.
(c) Flavouring:
   Balance to desired quantities by first simultaneously increasing sodium bicarbonate and potassium nitrate using a 3:1 ratio. If necessary continue balancing increasing microcrystalline wax.
(d) Potassium nitrate:
   Balance by first decreasing sodium bicarbonate to maintain the 3:1 ratio listed above. Then, if necessary, continue balancing by adding sorbitan monostearate and/or polysorbate 60 to desired levels followed by microcrystalline wax, last.
(e) Sorbitan monostearate:
   Increase polysorbate 60 using the same ratio first. Then, if needed, add microcrystalline wax for any further balancing requirements.
(f) Polysorbate 60:
   Balance by first adding microcrystalline wax. Then, if further balancing is essential, raise the amount of sorbitan monostearate next.
(g) Sodium saccharin:
   Balance by first increasing flavouring to desired amount. Next, if needed, add microcrystalline wax for any further balancing needs.
(h) Sodium Fluoride:
   Balance by increasing microcrystalline wax by the same amount.

Increasing From Optimal:
(a) Microcrystalline wax:
   Balance by first increasing, to desired levels, sodium bicarbonate and potassium nitrate using a 3:1 ratio. If further balancing is needed, lower sorbitan monostearate next followed by polysorbate 60 last.
(b) Sodium bicarbonate:
   Balance by first increase potassium nitrate to maintain 3:1 ratio. If any further balancing is required, reduce sorbitan monostearate second followed by polysorbate 60, last.
(c) Flavouring:
   Balance by first decreasing sorbitan monostearate and polysorbate 60 while maintaining same ratio, first. If needed, continue balancing by reducing microcrystalline wax next.
(d) Potassium nitrate:
   Balance by first increasing sodium bicarbonate to maintain 3:1 ratio. Then continue balancing, if necessary, by reducing flavouring next. If further balancing is still required reduce sorbitan monostearate and polysorbate 60, while maintaining the same ratio, last.
(e) Sorbitan monostearate:
   Balance by first decreasing polysorbate 60 using the same amount as sorbitan monostearate was increased. Next reduce microcrystalline wax to complete any balancing needs.
(f) Polysorbate 60:
   Balance by first decreasing sorbitan monostearate. Then, if needed, reduce microcrystalline wax second.
(g) Sodium saccharin:
   Balance by reducing flavouring as needed.
(h) Sodium Fluoride:
   Balance by reducing microcrystalline wax by the same amount.

Quantitative Formulation Balancing (Formulations 3 and 4)

First note: a ratio of about 3:1 sodium bicarbonate to potassium nitrate must at all times be maintained within these formulations. As such, decreasing or increasing one of these ingredient's overall percentage (W/W) will force the simultaneous decrease or increase of the other so as to maintain the 3:1 ratio mentioned above.

Second note: a formulation's optimal (W/W) figures are used as the base or reference line during any Quantitative Formulation Balancing. Consequently, any ingredients added or subtracted are referenced back to this starting point.

Thirdly, the preferential substances specified below are for illustrative purposes only and thus shall not be used to limit the scope of the Quantitative Formulation Balancing technique herein disclosed.

Decreasing From Optimal:
(a) Microcrystalline wax:
   Balance by increasing sorbitan monostearate as needed.
(b) Sodium bicarbonate:
   Balance by first decreasing potassium nitrate to maintain 3:1 ratio. Next, decrease flavouring to maintain emulsifiers. Finally, increase microcrystalline wax last to complete balancing.
(c) Flavouring:
   Balance by increasing sodium saccharin to suite taste, first. If necessary, add microcrystalline wax next.
(d) Potassium nitrate:
   Balance by first decreasing sodium bicarbonate to maintain 3:1 ratio. Then raise the amount of microcrystalline wax to complete balancing.
(e) Sorbitan monostearate:
   Balance by raising the amount of microcrystalline wax.
(f) Sodium saccharin:
   Balance by increasing the amount of flavouring.
(g) Sodium Fluoride:
   Balance by increasing microcrystalline wax by the same amount.

Increasing From Optimal:
(a) Microcrystalline wax:
   Balance by decreasing sorbitan monostearate as required.
(b) Sodium bicarbonate:
   Balance by first increasing potassium nitrate to maintain 3:1 ratio. Then increase microcrystalline wax as needed to complete task.
(c) Flavouring:
   Balance by first reducing sodium saccharin to suite taste. Next, lower the amount of microcrystalline wax to complete balancing.
(d) Potassium nitrate:
   Balance by first increasing sodium bicarbonate to maintain 3:1 ratio. Next reduce microcrystalline wax to complete the task.

(e) Sorbitan monostearate:
   Balance by decreasing the amount of microcrystalline wax.
(f) Sodium saccharin:
   Balance by reducing the amount of flavouring. Next increase the quantity of microcrystalline wax to finish task.
(g) Sodium Fluoride:
   Balance by reducing microcrystalline wax by the same amount.

Note also, that in order to help preserve chemical efficacy over extended periods and prevent chemical interactions during storage potassium nitrate, sodium bicarbonate, flavourings and other compounds may be encapsulated or microcoated. In addition, the encapsulating or microcoating materials used within each formulation should be the same in order to provide a simultaneous release and interaction of the chemical compounds used. Examples of some suitable encapsulating or microcoating substances may include, but are not limited to, ethylcellulose, methyl cellulose, sodium carboxymethyl cellulose, and other coating polymers or materials which can coat and preserve the ingredients until released by the mechanical action of flossing and or the usual enzymatic action provided by saliva.

Moreover, within a given formulation, each ingredient is permitted a range or a tolerance of about plus or minus five percent of the amount specified in order to allow for manufacturing variances. Thus, for example, sodium saccharin which has been herein specified as 0.40 percent (W/W) in all of the above formulations may actually range from 0.38 to 0.42 percent (W/W).

Finally, the four formulations detailed above may be prepared for and deposited upon various dental flosses by using conventional equipment, machinery, and production facilities in conjunction with the following method:

Staged Preparation Technique
(a) This method begins by first melting one or more binders, preferably microcrystalline wax, within a suitable container until they are liquified.
(b) Once these binders have been liquified, one or more first emulsifying agents, preferably sorbitan monostearate, are then added in a conventional manner to the liquified binders produced in step (a). The resulting composition is then mixed until visually homogenous.
(c) One or more second emulsifying agents, preferably polysorbate 60, are now added in a conventional manner to the liquified composition produced by step (b). The resulting composition is then, once again, mixed until visually homogenous. In formulations devoid of second emulsifying agents, such as in formulations 3 and 4 detailed above, this step is to be bypassed or otherwise deleted.
(d) A second container is now procured and in it is thoroughly mixed, using conventional methods and until visually homogenous, all other ingredients. These ingredients will include, but are not limited to, one or more polishing agents, preferably sodium bicarbonate; flavouring agents; desensitizing agents, preferably potassium nitrate; and sweetening agents, preferably sodium saccharin. If any fluoride based compounds or other ingredients are also to be used they are added, along with the others, at this time.
(e) Once the composition of step (d) has been prepared it is then added to the mixture produced by step (c) and thoroughly mixed, using conventional means, until visually homogenous.
(f) The resulting composition produced by step (e) is then uniformly applied to dental floss using conventional techniques.

For purposes of this disclosure the above six step method of producing a FEPD floss shall be herein called a Staged Preparation Technique. Using this method will assure the production of a high quality good tasting desensitizing floss time and time again. It must also be understood, that although this method is highly preferred other techniques are possible. As a result, the method provided herein should be considered illustrative and not limiting in nature.

Addendum

The following patents and other references, the entire contents of which are hereby incorporated by reference into this specification, offer the reader a supplementary appendage of current pharmacological and therapeutical information, flossing ingredients, components, and manufacturing methods. As such, this information may therefore be use, as required, in the production of all FEPD flosses herein described.

(1)
   U.S. Pat. No. 5,573,850
   Invented by: David V. Cunningham, Sheldon Kavesh, and Christopher P. Griffin.
   Issued: Nov. 12, 1996
(2)
   U.S. Pat. No. 5,560,377
   Invented by: Marion Donovan.
   Issued: Oct. 1, 1996
(3)
   U.S. Pat. No. 5,526,831
   Invented by: Sean G. Gilligan, Dermot T. Freeman, Larry J. Oliphant, Jeffrey S. Meessmann, Patrick J. Hanley, and Gerald S. Szczech.
   Issued: Jun. 18, 1996
(4)
   U.S. Pat. No. 5,423,337
   Invented by: Gary Ahlert.
   Issued: Jun. 13, 1995
(5)
   U.S. Pat. No. 5,357,990
   Invented by: Christopher H. Suhonen, and John A. Kaminski.
   Issued: Oct. 25, 1994
(6)
   U.S. Pat. No. 5,353,820
   Invented by: Christopher H. Suhonen, and Pedro L. Jusino.
   Issued: Oct. 11, 1994
(7)
   U.S. Pat. No. 5,220,932
   Invented by: Jacob M. Blass.
   Issued: Jun. 22, 1993
(8)
   U.S. Pat. No. 5,209,251
   Invented by: John P. Curtis, and James H. Kemp.
   Issued: May 11, 1993
(9)
   U.S. Pat. No. 5,098,711
   Invented by: Ira Hill, and Robert D. White.
   Issued: Mar. 24, 1992
(10)
   U.S. Pat. No. 4,548,219
   Invented by: Michael G. Newman.
   Issued: Oct. 22, 1985

(11)
Accepted Dental Therapeutics, 39th Edition,
Copyright 1982, by the American Dental Association,
211 E. Chicago Ave., Chicago, Ill., U.S.A., 60611.
Library of Congress Number: 74[2]-MCAT

(12)
Comprehensive Dental Hygiene Care, 4th Edition,
Written by: Irene R. Woodall,
Copyright 1993, by Mosby—Year Book, Inc.,
11830 Westline Industrial Drive, St. Louis, Mo., U.S.A., 63146.
ISBN: 0-8016-7019-5

(13)
The Merck Manual,
Executive Editor: Keryn A. G. Lane,
Copyright 1999, by Merck and Co., Inc.,
Whitehouse Station, N.J., U.S.A.,
Publisher: Gary Zelko.
ISBN: 0911910-10-7

(14)
Dental Clinics of North America,
Pharmacology and Therapeutics,
Issues: July 1984, and others,
Publisher: W. B. Saunders, 1 Goldthorn Avenue, Canada, N8Z 5T9,
ISSN: 0011-8532

(15)
Fenaroli's Handbook of Flavour Ingredients,
Written by: Prof. Dr. Giovanni Fenaroli,
Copyright 1971, by the Chemical Rubber Company,
18901 Cranwood Pkwy., Cleveland, Ohio, U.S.A., 44128.
Library of Congress Number: 72-152143

(16)
Flavor Technology, Profiles, Products, Applications,
Written by: Henry B. Heath, M. B. E., B. Pharm. (London),
Copyright 1978, Avi Publishing Company Incorporated,
Westport, Conn., U.S.A.
ISBN: 0-87005-258-9

Additional information regarding the subject of this invention can be found in the many books available to the public at libraries and technical centres or in the many patents and government publications currently available today.

In conclusion, the reader must also understand that the preceding description contains many specificities that should not be construed as limiting the scope of the invention but as merely providing illustrations of some of the presently preferred embodiments thereof. As a result, the scope of the invention should thus be determined by the appended claims and their legal equivalents rather than by the examples given.

The embodiments of the invention in which an exclusive property or privilege is claimed are defined as follows:

1. A flavour enhanced protective dental floss comprising a dental floss and a formulation, and wherein said flavour enhanced protective dental floss is made using a Staged Preparation Technique, and wherein said formulation is selected from the group consisting of:

Formulation Number One, wherein Formulation Number One comprises:
(a) one or more binders to a maximum of about 75 percent (W/W), with 41.0 percent (W/W) being optimal;
(b) one or more polishing agents to a maximum of about 30.0 percent (W/W), with 27.0 percent (W/W) being optimal;
(c) one or more flavouring agents to a maximum of about 25.0 percent (W/W), with 14.6 percent (W/W) being optimal;
(d) one or more dental desensitizing agents to a maximum of about 10.0 percent (W/W), with 9.0 percent (W/W) being optimal;
(e) one or more fir t emulsifying agents to a maximum of about 10.0 percent (W/W), with 5.0 percent (W/W) being optimal;
(f) one or more second emulsifying agents to a maximum of about 10.0 percent (W/W), with 3.0 percent (W/W) being optimal; and
(g) one or more sweetening agents to a maximum of about 1.0 percent (W/W), with 0.4 percent (W/W) being optimal;

Formulation Number Two, wherein Formulation Number Two comprises:
(a) one or more binders to a maximum of about 75 percent (W/W), with 40.78 percent (W/W) being optimal;
(b) one or more polishing agents to a maximum of about 30.0 percent (W/W), with 27.0 percent (W/W) being optimal;
(c) one or more flavouring agents to a maximum of about 25.0 percent (W/W), with 14.6 percent (W/W) being optimal;
(d) one or more dental desensitizing agents to a maximum of about 10.0 percent (W/W) with 9.0 percent (W/W) being optimal;
(e) one or more first emulsifying agents to a maximum of about 10.0 percent (W/W), with 5.0 percent (W/W) being optimal;
(f) one or more second emulsifying agents to a maximum of about 10.0 percent (W/W), with 3.0 percent (W/W) being optimal;
(g) one or more sweetening agents to a maximum of about 1.0 percent (W/W), with 0.4 percent (W/W) being optimal; and
(h) one or more flu ride compounds to a maximum of about 0.30 percent (W/W), with about 0.22 percent (W/W) being optimal;

Formulation Number Three, wherein Formulation Number Three comprises:
(a) one or more binders to a maximum of about 75 percent (W/W), with 55.6 percent (/W) being optimal;
(b) one or more polishing agents to a maximum of about 30.0 percent (W/W), with 27.0 percent (W/W) being optimal;
(c) one or more flavouring agents to a maximum of about 25.0 percent (W/W), with 3.0 percent (W/W) being optimal;
(d) one or more dental desensitizing agents to a maximum of about 10.0 percent (W/W), with 9.0 percent (W/W) being optimal;
(e) one or more fist emulsifying agents to a maximum of about 10.0 percent (W/W), with 5.0 percent (W/W) being optimal; and
(f) one or more sweetening agents to a maximum of about 1.0 percent (W/W), with 0.4 percent (W/W) being optimal Formulation Number Four, wherein Formulation Number Four comprises:
(a) one or more binders to a maximum of about 75 percent (W/W), with 55.38 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 3.0 percent (W/W) being optimal;

(d) one or more dental desensitizing agents to a maximum of about 10.0 percent (W/W), with 9.0 percent (W/W) being optimal;

(e) one or more first emulsifying agents to a maximum of about 10.0 percent (W/W), with 5.0 percent (W/W) being optimal;

(f) one or more sweetening agents to a maximum of about 1.0 percent (W/W), with 0.4 percent (W/W) being optimal; and (g) one or more fluoride compounds to a maximum of about 0.30 percent (W/W), with about 0.22 percent (W/W) being optimal.

2. The claim as recited in claim 1 a Quantitative Formulation Balancing technique is used to a just the formulation of the flavour enhanced protective dental floss.

3. The claim as recited in claim 2 wherein said polishing agent is a salt, and said desensitizing agent is a salt.

4. The claim as recited in claim 3 wherein said binder is microcrystalline wax, said polishing agent is sodium bicarbonate, said dental desensitizing agent is potassium nitrate, said first emulsifying agent is sorbitan monostearate, said second emulsifying agent is polysorbate 60, said sweetening agent is sodium saccharin, and said fluoride compound is sodium fluoride.

5. The claim as recited in claim 1 wherein said polishing agent is a salt, and said desensitizing agent is a salt.

6. The claim as recited in claim 5 wherein said binder is microcrystalline wax, said polishing agent is sodium bicarbonate, said dental desensitizing agent is potassium nitrate, said first emulsifying agent is sorbitan monostearate, said second emulsifying agent is polysorbate 60, said sweetening agent is sodium saccharin, and said fluoride compound is sodium fluoride.

7. A flavour enhanced protective dental floss comprising a dental floss and a formulation, and wherein the (W/W) ratio of polishing agents to desensitizing agents within said formulation is approximately 3 to 1, and wherein said formulation is selected from the group consisting of:

Formulation Number One, wherein Formulation Number One comprises:
(a) one or more binders to a maximum of about 75 percent (W/W), with 41.0 percent (W/W) being optimal;
(b) one or more polishing agents to a maximum of about 30.0 percent (W/W), with 2.0 percent (W/W) being optimal, and wherein said polishing agent are salts;
(c) one or more flavouring agents to a maximum of about 25.0 percent (W/W), with 14.6 percent (W/W) being optimal;
(d) one or more dental desensitizing agents to a maximum of about 10.0 percent (W/W), with 9.0 percent (W/W) being optimal, and wherein said dental desensitizing agents are salts;
(e) one or more first emulsifying agents to a maximum of about 10.0 percent (W/W), with 5.0 percent (W/W) being optimal;
(f) one or more second emulsifying agents to a maximum of about 10.0 percent (W/W), with 3.0 percent (W/W) being optimal; and
(g) one or more sweetening agents to a maximum of about 1.0 percent (W/W), with 0.4 percent (W/W) being optimal;

Formulation Number Two, wherein Formulation Number Two comprises:
(a) one or more binders to a maximum of about 75 percent (W/W), with 40.78 percent (W/W) being optimal;
(b) one or more polishing agents to a maximum of about 30.0 percent (W/W), with 2.0 percent (W/W) being optimal, and wherein said polishing agent are salts;
(c) one or more flavouring agents to a maximum of about 25.0 percent (W/W), with 1.6 percent (W/W) being optimal;
(d) one or more dental desensitizing agents to a maximum of about 10.0 percent (W/W) with 9.0 percent (W/W) being optimal, and wherein said dental desensitizing agents are salts;
(e) one or more first emulsifying agents to a maximum of about 10.0 percent (W/W), with 5.0 percent (W/W) being optimal;
(f) one or more second emulsifying agents to a maximum of about 10.0 percent (W/W), with 3.0 percent (W/W) being optimal;
(g) one or more sweetening agents to a maximum of about 1.0 percent (W/W), with 0.4 percent (W/W) being optimal; and
(h) one or more fluoride compounds to a maximum of about 0.30 percent (W/W), with about 0.22 percent (W/W) being optimal;

Formulation Number Three, wherein Formulation Number Three comprises:
(a) one or more binders to a maximum of about 75 percent (W/W), with 55.6 percent (W/W) being optimal;
(b) one or more polishing agents to a maximum of about 30.0 percent (W/W), with 27.0 percent (W/W) being optimal, and wherein said polishing agent are salts;
(c) one or more flavouring agents to a maximum of about 25.0 percent (W/W), with 3.0 percent (W/W) being optimal;
(d) one or more dental desensitizing agents to a maximum of about 10.0 percent (W/W), with 9.0 percent (W/W) being optimal, and wherein said dental desensitizing agents are salts;
(e) one or more first emulsifying agents to a maximum of about 10.0 percent (W/W), with 5.0 percent (W/W) being optimal; and
(f) one or more sweetening agents to a maximum of about 1.0 percent (W/W), with 0.4 percent (W/W) being optimal;

Formulation Number Four, wherein Formulation Number Four comprises:
(a) one or more binders to a maximum of about 75 percent (W/W), with 55.38 percent (W/W) being optimal;
(b) one or more polishing agents to a maximum of about 30.0 percent (W/W), with 27.0 percent (W/W) being optimal, and wherein said polishing agent are salts;
(c) one or more flavouring agents to a maximum of about 25.0 percent (W/W), with 3.0 percent (W/W) being optimal;
(d) one or more dental desensitizing agents to a maximum of about 10.0 percent (W/W), with 9.0 percent (W/W) being optimal, and wherein said dental desensitizing agents are salts;
(e) one or more first emulsifying agents to a maximum of about 10.0 percent (W/W), with 5.0 percent (W/W) being optimal;

(f) one or more sweetening agents to a maximum of about 1.0 percent (W/W), with 0.4 percent (W/W) being optimal; and (g) one or more fluoride compounds to a maximum of about 0.30 percent (W/W), with about 0.22 percent (W/W) being optimal.

8. The claim as recited in claim 7 wherein said flavour enhanced protective dental floss is made by using a Staged Preparation Technique.

9. The claim as recited in claim 8 wherein a Quantitative Formulation Balancing technique is used to a just the formulation of the flavour enhanced protective dental floss.

10. The claim as recited in claim 9 wherein said binder is microcrystalline wax, said polishing agent is sodium bicarbonate, said dental desensitizing agent is potassium nitrate, said first emulsifying agent is sorbitan monostearate, said second emulsifying agent is polysorbate 60, said sweetening agent is sodium saccharin, and said fluoride compound is sodium fluoride.

11. The claim as recited in claim 10 wherein said formulation further includes at least one, peroxide based compound, other polishing or abrading agent, pigmenting agent, encapsulating compound, microcoating compound, alone or in combination.

12. The claim as recited in claim 9 wherein said formulation further includes at least one, peroxide based compound, other polishing or abrading agent, pigmenting agent, encapsulating compound, microcoating compound, alone or in combination.

13. The claim as recited in claim 7 wherein a Quantitative Formulation Balancing technique is used to a just the formulation of the flavour enhanced protective dental floss.

14. The claim as recited in claim 13 wherein said binder is microcrystalline wax, said polishing agent is sodium bicarbonate, said dental desensitizing agent is potassium nitrate, said first emulsifying agent is sorbitan monostearate, said second emulsifying agent is polysorbate 60, said sweetening agent is sodium saccharin, and said fluoride compound is sodium fluoride.

15. The claim as recited in claim 14 wherein said formulation further includes at least one, peroxide based compound, other polishing or abrading agent, pigmenting agent, encapsulating compound, microcoating compound, alone or in combination.

16. The claim as recited in claim 13 wherein said formulation further includes at least one, peroxide based compound, other polishing or abrading agent, pigmenting agent, encapsulating compound, microcoating compound, alone or in combination.

17. The claim as recited in claim 7 wherein said binder is microcrystalline wax, said polishing agent is sodium bicarbonate, said dental desensitizing agent is potassium nitrate, said first emulsifying agent is sorbitan monostearate, said second emulsifying agent is polysorbate 60, said sweetening agent is sodium saccharin, and said fluoride compound is sodium fluoride.

18. The claim as recited in claim 17 wherein said formulation further includes at least one, peroxide based compound, other polishing or abrading agent, pigmenting agent, encapsulating compound, microcoating compound, alone or in combination.

19. The claim as recited in claim 7 wherein said formulation further includes at least one, peroxide based compound, other polishing or abrading agent, pigmenting agent, encapsulating compound, microcoating compound, alone or in combination.

20. A method for reducing dental plaques, caries, and dentinal hypersensitivity, in the interproximal and subgingival areas of the teeth, comprising the steps of:

(I) providing a dental floss;

(II) providing a formulation wherein said formulation is made using a A Staged Preparation Technique, and wherein a Quantitative Formulation Balancing technique is used to adjust the formulation of the flavour enhanced protective dental floss, and wherein said formulation is selected from the group consisting of:

Formulation Number One, wherein Formulation Number One comprises:

(a) one or more binders to a maximum of about 75 percent (W/W), with 41.0 percent (/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 14.6 percent (W/W) being optimal;

(d) one or more dental desensitizing agents to a maximum of about 10.0 percent (W/W), with 9.0 percent (W/W) being optimal;

(e) one or more first emulsifying agents to a maximum of about 10.0 percent (W/W), with 5.0 percent (W/W) being optimal;

(f) one or more second emulsifying agents to a maximum of about 10.0 percent (W/W), with 3.0 percent (W/W) being optimal; and (g) one or more sweetening agents to a maximum of about 1.0 percent (W/W), with 0.4 percent (W/W) being optimal;

Formulation Number Two, wherein Formulation Number Two comprises:

(a) one or more binders to a maximum of about 75 percent (W/W), with 40.78 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 14.6 percent (W/W) being optimal;

(d) one or more dental desensitizing agents to a maximum of about 10.0 percent (W/W) with 9.0 percent (W/W) being optimal;

(e) one or more first emulsifying agents to a maximum of about 10.0 percent (W/W), with 5.0 percent (W/W) being optimal;

(f) one or more second emulsifying agents to a maximum of about 10.0 percent (W/W), with 3.0 percent (W/W) being optimal;

(g) one or more sweetening agents to a maximum of about 1.0 percent (W/W), with 0.4 percent (W/W) being optimal; and (h) one or more fluoride compounds to a maximum of about 0.30 percent (W/W), with about 0.22 percent (W/W) being optimal;

Formulation Number Three, wherein Formulation Number Three comprises:

(a) one or more binders to a maximum of about 75 percent (W/W), with 55.6 percent (W/W) being optimal;

(b) one or more polishing agents to a maximum of about 30.0 percent (W/W), with 27.0 percent (W/W) being optimal;

(c) one or more flavouring agents to a maximum of about 25.0 percent (W/W), with 3.0 percent (W/W) being optimal;
(d) one or more dental desensitizing agents to a maximum of about 10.0 percent (W/W), with 9.0 percent (W/W) being optimal;
(e) one or more first emulsifying agents to a maximum of about 10.0 percent (W/W), with 5.0 percent (W/W) being optimal; and
(f) one or more sweetening agents to a maximum of about 1.0 percent (W/W), with 0.4 percent (W/W) being optimal;

(Formulation Number Four, wherein Formulation Number Four comprises:
(a) one or more binders to a maximum of about 75 percent (W/W), with 55.38 percent (W/W) being optimal;
(b) one or more polishing agents to a maximum of about 30.0 percent (W/W), with 27.0 percent (W/W) being optimal;
(c) one or more flavouring agents to a maximum of about 25.0 percent (W/W), with 3.0 percent (W/W) being optimal;
(d) one or more dental desensitizing agents to a maximum of about 10.0 percent (W/W), with 9.0 percent (W/W) being optimal;
(e) one or more first emulsifying agents to a maximum of about 10.0 percent (W/W), with 5.0 percent (W/W) being optimal;
(f) one or more sweetening agents to a maximum of about 1.0 percent (W/W), with 0.4 percent (W/W) being optimal; and
(g) one or more fluoride compounds to a maximum of about 0.30 percent (W/W), with about 0.22 percent (W/W) being optimal;

(III) contacting said formulation with said dental floss by incorporating said formulation therein or as a topical applicant in order to thereby produce a flavour enhanced protective dental floss; and (IV) flossing with said flavour enhanced protective dental floss to thereby reduce said plagues, caries, and dentinal hypersensitivity.

21. A method for the production of dental floss formulations using a Staged Preparation Technique wherein said Staged Preparation Technique comprises the following steps:
(a) This method b gins by first melting one or more binders, preferably microcrystalline wax, within a suitable container until they are liquified
(b) Once these binders have been liquified, one or more first emulsifying agents, preferably sorbitan monostearate, are then added in a conventional manner to the liquified binders produced in step (a); The resulting composition is then mixed until visually homogenous;
(c) One or more second emulsifying agents, preferably polysorbate 60, are now added in a conventional manner to the liquified composition produced by step (b); The resulting composition is then, once again, mixed until visually homogenous; In formulations devoid of second emulsifying agents, such as in formulations 3 and 4 detailed above, this step is to e bypassed or otherwise deleted;
(d) A second container is now procured and in it is thoroughly mixed, using conventional methods and until visually homogenous, all other ingredients; These ingredients will include, but are not limited to, one or more polishing agents, preferably sodium bicarbonate; flavouring agents; desensitizing agents, preferably potassium nitrate; and sweetening agents, preferably sodium saccharin; If any fluoride based compounds or there ingredients are also to be used they are added, along with the others, at this time;
(e) Once the composition of step (d) has been prepared it is then added to the mixture produced by step (c) and thoroughly mixed, using conventional means, until visually homogenous;
(f) The resulting composition produced by step (e) is then uniformly applied to dental floss using conventional techniques.

* * * * *

UNITED STATES PATENT AND TRADEMARK OFFICE
CERTIFICATE OF CORRECTION

PATENT NO. : 6,619,300 B2
DATED : September 16, 2003
INVENTOR(S) : Robert Victor Marcon and Lawrence Wayne Nash It is certified that error appears in the above-identified patent and that said Letters Patent is hereby corrected as shown below:

Column 10,
Line 57, Formulation Number Two (d), delete "10.0 percent (W/W)" with" and substitute -- 10.0 percent (W/W), with -- therefor.
Line 64, Formulation Number Two (f), delete "being optimal; and" and substitute -- being optimal; and -- therefor.
Line 67, Formulation Number Two (g), delete "being optimal." and substitute -- being optimal; and -- therefor.

Column 11,
Line 38, Formulation Number Four (e), delete "being optimal; and" and substitute -- being optimal; and -- therefor.
Line 42, Formulation Number Four (f), delete "being optimal." and substitute -- being optimal; and -- therefor.

Column 17,
Line 10, delete "St. Louis, Mo" and substitute -- St. Louis, Missouri -- therefor.

Column 18,
Line 10, Formulation Number One (e), delete "fir t" and substitute -- first -- therefor.
Line 31, Formulation Number Two (d), delete "10.0 percent (W/W)" with" and substitute -- 10.0 percent (W/W), with -- therefor.
Line 40, Formulation Number Two (h), delete "flu ride" and substitute -- fluoride -- therefor.
Line 48, Formulation Number Three (a), delete "56.6 percent (/W)" and substitute -- 55.6 percent (W/W), -- therefor.
Line 59, Formulation Number Three (e), delete "fist" and substitute -- first -- therefor.
Line 64, Formulation Number Three (f), delete "being optimal" and substitute -- being optimal; -- therefor.

UNITED STATES PATENT AND TRADEMARK OFFICE
CERTIFICATE OF CORRECTION

| | |
|---|---|
| PATENT NO. | : 6,619,300 B2 |
| DATED | : September 16, 2003 |
| INVENTOR(S) | : Robert Victor Marcon and Lawrence Wayne Nash |

It is certified that error appears in the above-identified patent and that said Letters Patent is hereby corrected as shown below:

Column 19,
Line 18, delete "in claim 1 a" and substitute -- in claim 1 wherein a -- therefor.
Line 19, delete "a just" and substitute -- adjust -- therefor.
Line 49, Formulation Number One (b), delete "2.0 percent "(W/W)" and substitute -- 27.0 percent (W/W) -- therefor.
Line 50, Formulation Number One (b), delete "polishing agent"and substitute -- polishing agents -- therefor.

Column 20,
Line 7, Formulation Number Two (b), delete "2.0 percent (W/W)" and substitute -- 27.0 percent (W/W), with -- therefor.
Line 8, Formulation Number Two (b), delete "polishing agent" and substitute -- polishing agents -- therefor.
Line 11, Formulation Number Two (c), delete "1.6 percent (W/W)" and substitute -- 14.6 percent (W/W), -- therefor.
Line 14, Formulation Number Two (d), delete "10.0 percent (W/W)" and substitute -- 10.0 percent (W/W), -- therefor.
Line 36, Formulation Number Three (b), delete "said polishing agent"and substitute -- said polishing agents -- therefor.

Column 21,
Lines 11 and 32, delete "a just" and substitue -- adjust -- therefor.

Column 22,
Line 6, delete "using a  A Staged" and substitute -- using a Staged -- therefor.
Line 14, Formulation Number One (a), delete "41.0 percent (/W)" with" and substitute -- 41.0 percent (W/W), -- therefor.
Line 46, Formulation Number Two (d), delete "10.0 percent (W/W)" with" and substitute -- 10.0 percent (W/W), -- therefor.

UNITED STATES PATENT AND TRADEMARK OFFICE
CERTIFICATE OF CORRECTION

PATENT NO. : 6,619,300 B2
DATED : September 16, 2003
INVENTOR(S) : Robert Victor Marcon and Lawrence Wayne Nash It is certified that error appears in the above-identified patent and that said Letters Patent is hereby corrected as shown below:

Column 23,
Line 13, Formulation Number Four (d), delete "(Formulation" and substitute
-- Formulation -- therefor.

Column 24,
Line 5, delete "b gins" and substitute -- begins -- therefor.
Line 7, delete "are liquified" and substitute -- are liquified; -- therefor.
Line 20, delete "to e bypassed" and substitute -- to be bypassed -- therefor.
Line 37, delete "visually homogenous;" and substitute -- visually homogenous; and -- therefor.

Signed and Sealed this

Third Day of August, 2004

JON W. DUDAS
*Acting Director of the United States Patent and Trademark Office*